United States Patent [19]

Ueno et al.

[11] Patent Number: 5,194,429
[45] Date of Patent: Mar. 16, 1993

[54] OCULAR HYPOTENSIVE AGENTS

[75] Inventors: Ryuzo Ueno; Ryuji Ueno, both of Nishinomiya; Tomio Oda, Sanda, all of Japan

[73] Assignee: K.K. Ueno Seiyaku Oyo Kenkyujo, Osaka, Japan

[21] Appl. No.: 615,515

[22] Filed: Nov. 19, 1990

Related U.S. Application Data

[62] Division of Ser. No. 414,331, Sep. 29, 1989, abandoned.

[30] Foreign Application Priority Data

Oct. 1, 1988 [JP] Japan ................................. 63-248720
Oct. 1, 1988 [JP] Japan ................................. 63-248721

[51] Int. Cl.$^5$ .................. A61K 31/695; A61K 31/35; A61K 31/215; A61K 31/19
[52] U.S. Cl. ...................................... 514/63; 514/451; 514/530; 514/573; 514/913
[58] Field of Search ................. 514/63, 530, 451, 573, 514/913

[56] References Cited

U.S. PATENT DOCUMENTS

| | | | |
|---|---|---|---|
| 4,128,713 | 12/1978 | Schneider et al. | 542/426 |
| 4,131,738 | 12/1978 | Smith | 560/121 |
| 4,599,353 | 7/1986 | Bito | 514/530 |
| 4,883,819 | 11/1989 | Bito | 514/573 |

FOREIGN PATENT DOCUMENTS

| | | |
|---|---|---|
| 0093380 | 11/1983 | European Pat. Off. . |
| 0253094 | 11/1988 | European Pat. Off. . |
| 0308135 | 3/1989 | European Pat. Off. . |
| 0364417 | 6/1989 | European Pat. Off. . |
| 0330511 | 8/1989 | European Pat. Off. . |
| 2110335 | 6/1972 | France . |

OTHER PUBLICATIONS

Woodward. Opthalmic Res 21 428 (1989).
Acta Pharmaceutica Sinica, vol. 16, No. 5 (May 1981).
Invest. Opthalmol. Visual Sci., vol. 16, No. 12, Dec. 1977, pp. 1125–1134.

Primary Examiner—Frederick E. Waddell
Assistant Examiner—Zohreh A. Fay
Attorney, Agent, or Firm—Sughrue, Mion, Zinn, Macpeak & Seas

[57] ABSTRACT

The present invention relates to an ocular hypotensive composition and a composition for treatment of glaucoma which comprising an amount of 20-substituted-PGs or 20-substituted-15-keto-PGs effective as an ocular hypotensive agent; these compounds exhibit no or little side effects such as transient ocular hypertensive response, hyperemia of conjunctiva or of iris, dacryops, lema, closed eye and the like.

13 Claims, No Drawings

OCULAR HYPOTENSIVE AGENTS

This is a divisional of application Ser. No. 07/414,331 filed Sep. 29, 1989, now abandoned.

BACKGROUND OF THE INVENTION

The present invention relates to ocular hypotensive agents or agents used for treatment of glaucoma which contains prostaglandins or 15-keto-prostaglandins, in which the carbon atom of the 20-position is substituted with a hydrocarbon group.

Prostaglandins (hereinafter referred to as PGs) are the name given to the group of fatty acids which show various physiological activities and contained in human and animal tissues and organs. PGs essentially contain the prostanoic acid skeleton of the following formula:

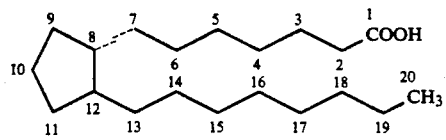

and some synthetic products may contain the above skeleton with some modification.

PGs are classified into several types according to their five-membered ring, for example,

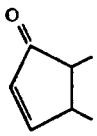
prostaglandins of the A series (PGAs):

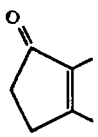
Prostaglandins of the B series (PGBs):

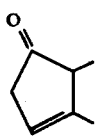
Prostaglandins of the C series (PGCs):

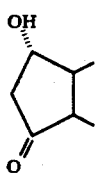
Prostaglandins of the D series (PGDs):

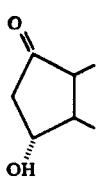
Prostaglandins of the E series (PGEs):

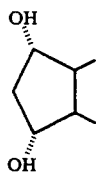
Prostaglandins of the F series (PGFs):

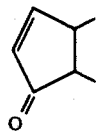
Prostaglandins of the J series (PGJs):

and the like. Further, they are classified into $PG_1s$ containing 5,6-single bond:

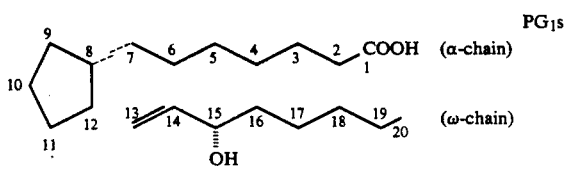

$PG_2s$ containing 5,6-double bond:

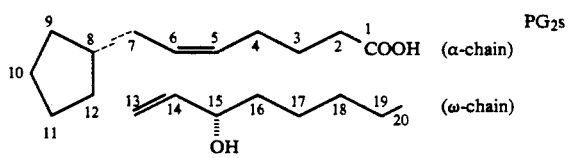

and $PG_3s$ containing 5,6- and 17,18-double bonds:

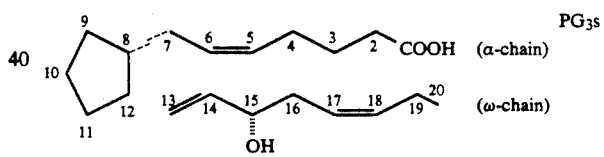

PGs are known to have various pharmacological and physiological activities, for example, vasodilation, induction of inflammation, platelet aggregation, contraction of uterine muscle, enteron contraction and the like. However, PGs also possesses various other activities, therefore there are some problems to use them as medicines. That is, when PGs are administered to obtain a single pharmaceutical activity, they often exhibit other activities as side effects. Accordingly, the investigations of PGs as a medicine have aimed to enhance the emergency of the main pharmaceutical activity. However, these investigations have been insufficient.

Among PGs, for example, PGAs, PGDs, PGEs, PGFs are known to possess ocular hypotensive potency.

For example, there is described in Japanese Patent Application KOKAI No. 1418/1984 claiming a priority based on U.S. Ser. No. 374,165(1982) by Laszlo Z. Bite that $PGF_2$ has a high ocular hypotensive activity, and 15-keto-$PGF_2$ has also it though a very little; and further in Japanese Patent Application KOKAI No. 66122/1988 claiming priorities based on three U.S. Ser. Nos. 839,056 (1986), 892,387(1986) and 022,046 (1987)

that PGA, PGB and PGC can be used for a treatment of glaucoma.

However, when topical application of these PGs, topically to rabbit eyes, they are accompanied with transient ocular hypertensive response, and still pronounced conjunctival and iridal hyperemia, and further side effects such as lacrimation, eye mucus, lid closure and the like are observed. Accordingly, there are some problems when PGs are used as remedies for glaucoma or ocular hypotensive agents.

SUMMARY OF THE INVENTION

It has been found that PGs in which the number of the carbon atom in the ω-chain is increased, for instance, PGs in which the carbon atom of the 20-position is substituted with a hydrocarbon group (referred to as 20-substituted PGs hereinafter) or 15-keto-PGs in which the carbon atom of the 20-position is substituted with a hydrocarbon group (referred to as 20-substituted-15-keto-PGs hereinafter) cause intraocular pressure reduction without any transient ocular hypertensive response that PGs usually show. Further, they possess enhanced ocular hypotensive potency, and exhibit ocular hypotensive effect without transient ocular hypertensive response, and with absolutely no or extremely reduced side effects such as hyperemia of conjunctiva or of iris, dacryops, lema, closed eye and the like.

DETAILED DESCRIPTION OF THE INVENTION

The present invention provides an ocular hypotensive composition or a composition for treatment of glaucoma, which contains PGs or 15-keto-PGs, in which the carbon atom of the 20-position is substituted with a hydrocarbon group (i.e. 20-substituted-PGs or 15-keto-20-substituted-PGs) as active ingredients.

In this description, 20-substituted-PGs and 20-substituted-15-keto-PGs are expressed as follows. That is, in the both, the carbons constituting the α-chain, ω-chain and 5-membered ring are numbered according to the basic skeleton as follows:

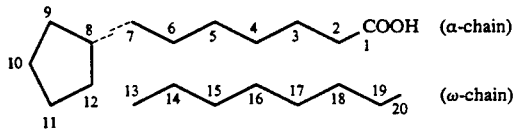

That is, in the basic skeleton, the constituent carbon atoms are numbered in such a way that the carbon atom in carboxylic acid is C-1, and the α-chain contains C-2~C-7, the number increasing toward the ring, the five-membered ring contains C-8~C-12, and the ω-chain contains C-13~C20. When the carbons of the α-chain are fewer, the numbers of the carbons ensuing C-2 should be properly shifted, and when more than 7, the compound is named provided that the carbon at the 2 position has a substituent instead of the carboxyl group (at the 1 position) and when more than 8, the carbon atoms at the 21 position and thereafter should be regarded as a substituent. As configuration, it is considered according to that of the above essential skeleton unless otherwise described.

For example, PGD, PGE and PGF mean compounds having a hydroxyl group at the 9 and/or 11 positions. In the present intention, PGs include those having other group instead of the hydroxyl group on the 9 and/or 11 positions, they being named as 9-dehydroxy-9-substituted or 11-dehydroxy-11-substituted compounds. 20-substituted-PGs or 20-substituted-15-keto-PGs used in the present invention may be PGs wherein 20-substituted $PG_1s$ or 20-substituted-15-keto-$PG_1s$ containing a 5,6-single bond; 20-substituted-$PG_2s$ or 20-substituted-15-keto-$PG_2s$ containing a 5,6-double bond, 20-substituted-$PG_3s$ or 20-substituted-15-keto-$PG_3s$ containing both 5,6- and 17,18-double bonds may be used.

The typical examples of the PGs used in the present invention are shown below:

A toner for developing electrostatic latent images comprising at least
  a resin,
  a colorant, and
  an imidazole derivative represented by the general formula XI] below;
20-substituted or 20-substituted-15-keto-$PGA_1s$,
20-substituted or 20-substituted-15-keto-$PGA_2s$,
20-substituted or 20-substituted-15-keto-$PGA_3s$,
20-substituted or 20-substituted-15-keto-$PGB_1s$,
20-substituted or 20-substituted-15-keto-$PGB_2s$,
20-substituted or 20-substituted-15-keto-$PGB_3s$,
20-substituted or 20-substituted-15-keto-$PGC_1s$,
20-substituted or 20-substituted-15-keto-$PGC_2s$,
20-substituted or 20-substituted-15-keto-$PGC_3s$,
20-substituted or 20-substituted-15-keto-$PGD_1s$,
20-substituted or 20-substituted-15-keto-$PGD_2s$,
20-substituted or 20-substituted-15-keto-$PGD_3s$,
20-substituted or 20-substituted-15-keto-$PGE_1s$,
20-substituted or 20-substituted-15-keto-$PGE_2s$,
20-substituted or 20-substituted-15-keto-$PGE_3s$,
20-substituted or 20-substituted-15-keto-$PGF_1s$,
20-substituted or 20-substituted-15-keto-$PGF_2s$,
20-substituted or 20-substituted-15-keto-$PGF_3s$,
20-substituted or 20-substituted-15-keto-$PGJ_1s$,
20-substituted or 20-substituted-15-keto-$PGJ_2s$,
20-substituted or 20-substituted-15-keto-$PGJ_3s$ or
the like. Derivatives, esters or salts of these PGs may be used, too.

These 20-substituted-PGs or 20-substituted-15-keto-PGs show strong ocular hypotensive potency without showing transient ocular hypertensive response as well as side effects such as pronounced conjunctival or iridal hyperemia, lacrimation, lid closure and the like, or extremely reduced, if any. Accordingly, these 20-substituted PGs or 20-substituted-15-keto-PGs are extremely effective as ocular hypotensive agents. Further, depending on such ocular hypotensive effect, they may be used for glaucoma therapy.

In the present invention, the ocular hypotensive effect of 20-substituted PGs or 20-substituted-15-keto-PGs may be especially remarkable in prostaglandins of the general formula:

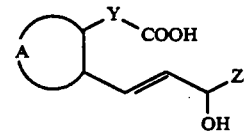

[I]

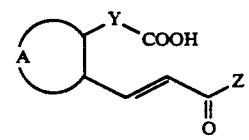

[II]

[wherein, A is

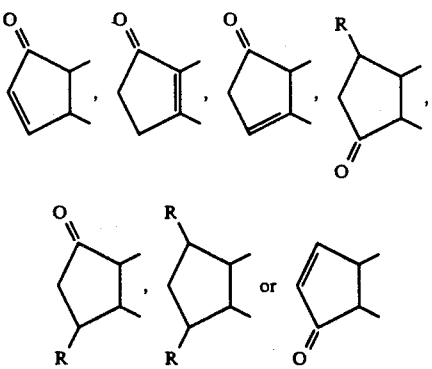

(in which R is hydroxyl, hydroxyalkyl or alkyl); Y is a saturated or unsaturated $C_{2-6}$ hydrocarbon chain (a part of the carbon atoms constituting the hydrocarbon chain may form a carbonyl group, and the hydrocarbon chain may be substituted with one or more atoms or groups); Z is a $C_{5-10}$ saturated or unsaturated aliphatic, alicyclic, aralkyl or aromatic hydrocarbon,(the hydrocarbon may be substitued with one or more atoms or groups)] or physiologically acceptable salts derived from the general formula [I] or those having an esterified carboxyl group.

A saturated or unsaturated $C_{2-6}$ hydrocarbon chain Y includes a straight hydrocarbon chain such as an alkyl, alkenyl, alkynyl and the like. Especially, a hydrocarbon chain with 6 carbons is preferred.

The examples of an unsaturated hydrocarbon chain Y include, for example, PGs wherein carbons at the 2–3 positions or the 5–6 positions are unsaturatedly bonded.

Some of the carbons forming the hydrocarbon chain Y may form a carbonyl group. The typical example includes 6-keto-PG$_1$s wherein the carbon at the 6 position constituting a carbonyl group.

The hydrocarbon chain Y may be substituted with one or more atoms or groups. Such atoms or groups include, for example, a halogen atom such as a fluorine, chlorine or bromine atom; an alkyl group such as methyl, ethyl; a hydroxyl group. The typical example is PGs having one or more alkyl groups at the 3 position.

The hydrocarbon group Z is a $C_5 \sim C_{10}$ alkyl group, preferably $C_5 \sim C_9$ alkyl group, which may have one or more branch(es). Preferable examples of the hydrocarbon group Z is methyl, ethyl, n-propyl, isopropyl, n-butyl, t-butyl and the like, and most preferable one is an alkyl group having no branch.

The hydrocarbon Z may be substituted with one or more atoms or groups. Such atoms or groups include a halogen atom such as a fluorine, chlorine or bromine atom; an alkyl group such as a methyl, ethyl, isopropyl or isopropenyl group; an alkoxy group such as a methoxy or ethoxy group; a hydroxyl group; a phenyl group; a phenoxy group and the like. The position of the substituent atom(s) or group(s) may not be limited, but typically, they may be at 16, 17, 19 and/or 20 position in the ω-chain. Particularly, compounds having one or two same or different atoms at the 16 position, for example, a halogen atom such as a fluorine atom or a substituent, for example, an alkyl group such as a methyl, ethyl, hydroxyl phenyl which may contain one or more substituents, benzyl, phenoxy, or cycloalkyl group such as a cyclopentyl or cyclohexyl group which contains the 16 position as a constituent; an alkyl group such as methyl at the 17 or 19 position: an alkyl group such as a methyl, ethyl, isopropyl, isopropenyl or alkoxy group such as a methoxy, ethoxy or propoxy group at the 20 position are preferred.

PGs may include the compounds PGD, PGE, PGF which contain a hydroxyl group at the 9 and/or 11 position. In the present specification, PGs further include the compounds having a hydroxyalkyl or alkyl group instead of the hydroxyl group at the 9 and/or 11 position. Accordingly, the 20-substituted-PGs or 20-substituted-15-keto-PGs of the present invention include the compound of the general formula [I], wherein R is a hydroxyl, hydroxyalkyl or alkyl group. Such hydroxyalkyl group preferably include a hydroxymethyl or 1-hydroxyethyl, 2-hydroxyethyl or 1-methyl-1-hydroxyethyl group. As the alkyl group, a lower alkyl group, especially a methyl or ethyl group are preferred.

The configuration of R for the carbon at the 9 and/or 11 position may be an $\alpha$, $\beta$ or mixture thereof.

PGs of the present invention may be salts or those with an esterified carboxyl group. Such salts include physiologically acceptable salts, for example, those of an alkali metal such as sodium, potassium; those of an alkaline earth metal such as calcium, magnesium; those of physiologically acceptable an ammonium or amine salt such as ammonia, methylamine, dimethylamine, cyclopentylamine, benzylamine, piperidine, monoethanolamine, diethanplamine, monomethylmonoethanolamine, tromethamine, lysine, tetralkylammonium salt and the like. Such an ester includes, for a example, methyl, ethyl, propyl, butyl, isopropyl, t-butyl, 2-ethylhexyl, straight or branched-chain alkyl ester which may contain an unsaturated bond; for example, ester having an alicyclic group such as a cyclopropyl, cyclopentyl or cyclohexyl group; an ester containing an aromatic group such as a benzyl or phenyl group (wherein the aromatic group may contain one or more substituents); a hydroxyalkyl or alkoxyalkyl ester such as a hydroxyethyl, hydroxyisopropyl, polyhydroxyisopropyl, methoxyethyl, ethoxyethyl or methoxyisopropyl group; an alkylsilyl ester e.g., a trimethylsilyl or triethylsilyl ester; a tetrahydropyranyl ester.

Preferred esters include, for example, a straight or branched lower alkyl ester such as a methyl, ethyl, propyl, n-butyl, isopropyl or t-butyl ester; or a benzyl ester; a hydroxyalkyl ester such as a hydroxyethyl or hydroxyisopropyl ester.

The carboxyl group at the 1 position of 20-substituted-PGs or 20-substituted-15-keto-PGs of the present invention may be any of the above described groups. Among them, esters, especially the $C_{1-4}$ alkyl ester, especially isopropyl ester are preferred considering emergency of ocular hypotensive effect.

20-substituted-PGs or 20-substituted-15-keto-PGs of the present invention may include the isomers of the above compounds. Examples of such isomers include keto-hemiacetal tautomers between the $C_6$-carbonyl and $C_9$-hydroxyl or optical isomers; geometrical isomers and the like.

The mixture of the isomers, for example, those of racemic body, tautomers of hydroxyl compound and hemiacetals may show similar effect as that shown by the respective compound.

In the present invention, especially preferred 20-substituted-PGs or 20-substituted-15-keto-PGs may contain a 5,6-single or double bond, or a carbonyl group at the 6 position carbon atom. Another preferred groups are 20-substituted or 20-substituted-15-keto-PGs wherein the carbon atom at the 16 position may be substituted with a halogen atom or an alkyl group.

Particularly, the compounds having a $C_{1-4}$ alkyl, for example, a methyl, ethyl, propyl or butyl group at the 20 position, that is, having a prolonged ω-chain show enhanced ocular hypotensive effect with little side effects such as hyperemia. Accordingly, such compounds are preferred.

In the present invention, PGs are named according to the prostanoic acid skeleton. If named according to IUPAC, for example, $PGE_1$ corresponds to 7-[(1R,2R,3R)-3-hydroxy-2-[(E)-(3S)-3-hydroxy-1-octenyl]-5-oxo-cyclopentyl]heptanoic acid; $PGE_2$, (Z)-7-[(1R,2R,3R)-3-hydroxy-2-[(E)-(3S)-3-hydroxy-1-octenyl]-5-oxo-cyclopentyl]-hept-5-enoic acid; 20-ethyl-$PGE_1$ is 7-{(1R,2R,3R)-3-hydroxy-2-[(E)-(3S)-3-hydroxy-1-decenyl]-5-oxo-cyclopentyl)}-heptanoic acid, and 15-keto-20-ethyl-$PGE_1$ is 7-{(1R,2R,3R)-3-hydroxy-2-[(E)((3S)-3-oxo-1-decenyl]-5-oxo-cyclopentyl}-heptanoic acid. $PGF_1α$ corresponds to 7-[(1R,2R,3R,5S)-3,5-dihydroxy-2-[(E)-(3S)-3-hydroxy-1-octenyl]-cyclopentyl]-heptanoic acid; $PGF_2α$, (Z)-7-[(1R,2R,3R,5S)-3,5-dihydroxy-2-[(E)-(3S)-3-hydroxy-1-octenyl]-cyclopentyl]-5-heptenoic acid; therefore, 20-ethyl-$PGF_1α$ is 7-[(1R,2R,3R,5S)-3,5-dihydroxy-2{(E)-(3S)-3-hydroxy-1-decenyl}-cyclopentyl]-heptanoic acid and 15- keto-20-ethyl-$PGF_1α$ is 7-[(1R,2R,3R,5S)-3,5-dihydroxy-2{(E)-(3S)-3-oxo-1-decenyl}-cyclopentyl]-heptanoic acid. $PGF_2α$ is (Z)-7-[(1R,2R,3R,5S)-3,5-dihydroxy-2{(E)-(3S)-3-hydroxy-1-octenyl}-cyclopentyl]-5-heptenoic acid and 15-keto-20-ethyl-$PGF_2α$ is (Z)-7-[(1R,2R,3R,5S)-3,5-dihydroxy-2{(E)-(3S)-3- oxo-1-octenyl}-cyclopentyl]-5-heptenoic acid. Other PGs may also be named in the same way.

In the process for preparing 20-substituted-PGs: A commercially available (−)-Corey lactone, which is used as a starting material, is subjected to Collins oxidation to give an aldehyde. The aldehyde is allowed to react with dimethyl (2-oxoalkyl)phosphonate anion which has a desirable length of alkyl group to give an α,β-unsaturated ketone (in order to obtain 20-methyl-PGs disethyl(2-oxooctyl)phosphonate anion is used).

The obtained α,β-unsaturated ketone was reduced using sodium borohydride to give α,β-unsaturated hydroxyl compound, the hydroxyl group of which is protected with THP (see Synthetic Chart I). The precursor of 20-substituted-PGs introduced with ω-chain obtained from the above process can be converted to 20-substituted-PGs according to a general process for production of PGs.

15-Keto-20-substituted-PGs can be prepared by reacting the carbonyl group of the α,β-unsaturated ketone obtained in the process as described in the production of 20-substituted-PGs with diols to protect it as ketal, and the p-phenylbenzoyl group is removed from the resultant to give an alcohol. The hydroxyl group of the alcohol is protected with dihydropyran to give a tetrahydropyranyl ether. In the above process a precursor of the 15-keto-20-substituted-PGs can be obtained (see Synthetic Chart II).

PGs containing a methyl group instead of a hydroxy group at the 11 position may be obtained as follows: PGA obtained by Jones oxidation of the hydroxy group at the 9 position of the 11-tosylate is allowed to react with a dimethyl copper complex to give 11-dehydroxy-11-methyl-PGE. Alternatively, an alcohol obtained after elimination of p-phenylbenzoyl group is converted to a tosylate. An unsaturated lactone obtained by DBU treatment of the tosylate is converted to a lactol. After introduction of an α-chain using Wittig reaction, the resulting alcohol (9 position) is oxidized to give PGA. PGA is allowed to react with dimethyl copper complex to give 11-dehydroxy-11-methyl-PGE. The resultant is reduced using sodium borohydride and the like to give 11-dehydroxy-11-methyl-PGF.

PGs containing a hydroxymethyl group instead of a hydroxyl group at the 11 position is obtained as follow: 11-dehydroxy-11-hydroxymethyl-PGE is obtained by a benzophenone-sensitized photoaddition of methanol to PGAs. The resultant is, for example, reduced using sodium borohydride to give 11-dehydroxy-11-hydroxymethyl-PGFs.

16-Fluoro-PGs may be obtained using a dimethyl (3-fluoro-2-oxoalkyl)phosphonate anion in the preparation of an α,β-unsaturated ketone. Similarly, 19-methyl-PGs may be obtained using a dimethyl (6-methyl-2-oxoalkyl)phosphonate anion.

The preparations in the present invention are not construed to be limited to them, and suitable means for protection, oxidation, reduction and the like may be employed.

20-substituted-PGs or 20-substituted-15-keto-PGs of the present invention can be used as remedies for animal and human, and, in general, used for systemic or local application by oral administration, intravenous injection, subcutaneous injection, suppository, collyrium, oculentum and the like. The dosage varies depending on animals, human, age, weight, conditions, therapeutic effect, administration route, treatment time and the like.

The solid composition for oral administration of the present invention includes tablets, preparations, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain additives other than an inactive diluent, for example, a lubricant such as magnesium stearate; disintegrant such as fibrous calcium gluconate; a stabilizer such as etherified cyclodextrin, for example, α,β- or γ-cyclodextrin, dimethyl-α-, dimethyl-β-, trimethyl-β- or hydroxypropyl-β-cyclodextrin, branched cyclodextrin such as glucosyl-, maltosyl-cyclodextrin, formylated cyclodextrin, cyclodextrin containing sulfur, mitthoprotol, phospholipid and the like. When the above cyclodextrins are used, an inclusion compound with cyclodextrins may be sometimes formed to enhance stability. Alternatively, a phospholipid may be sometimes used to form a liposome, resulting in enhanced stability.

Tablets or pills may be coated with film soluble materials in the stomach or intestine such as sugar, gelatin, hydroxypropyl cellulose, hydroxypropylmethyl cellulose phthalate and the like, or with more than two layers. Further, they may be formed as capsules with absorbable substances such as gelatin.

A liquid composition for oral administration may contain a pharmaceutically acceptable emulsion, solution, suspension, syrup, elixir as well as a generally used inactive diluent, for example, purified water, ethanol and the like. Such a composition may contain, in addition to the inactive diluent, adjuvants such as wetting agents and suspensions, sweetening agents, flavoring agents, preservatives and the like.

Other compositions for oral administration include a spray formulated by known method, which may contain one or more active ingredients.

Injection for parenteral administration according to the present invention includes a steril, agueous or nonaqueous solution, suspension, emulsion and the like.

A diluent for such an aqueous solution and suspension includes, for example, injectable distilled water, physiological saline and Ringer's solution.

A diluent for non-aqueous solution and suspension includes, for example, propylene glycol, polyethylene glycol, vegetable oil such as olive oil, alcohols such as ethanol, polysorbate and the like. Such a composition may contain adjuvants such as preservatives, wetting agents, emulsifiers, dispersants, stabilizers and the like. These are sterilized, for example, by filtration through a bacteria-holding filter, compounding with germicides, gas sterilization or radio-sterilization. These may be used by preparing a sterile solid composition and dissolving in sterile water or sterile solvent for injection before use.

The collyrium according to the present invention may include a sterile aqueous or non-aqueous solution, suspension and the like. The diluent for such an aqueous solution or suspension includes, for example, distilled water or a physiological saline. The diluent for the nonaqueous solution or suspension may include an edible oil, liquid paraffin, mineral oil, propylene glycol, p-octyldodecanol and the like. Further, in order to make isotonic to tears, isotonic agents such as sodium chloride, benzalkonium chloride, phedrine chloride, procaine chloride, chloram phenicol, sodium citrate, or in order to maintain the pH value constant, buffer such as a borate or phosphate buffer may be used. Moreover, stabilizers such as sodium sulfite, sodium.carbonate, EDTA, propylene glycol; thickening agents such as glycerin, carboxymethyl cellulose, carboxyvinyl polymer; diluents such as polysorbate, macrogols, alminum monostearate; preservatives such as paraben, benzyl alcohol, sorbic acid; and further resolvents, vehicles may be compounded. These may be sterilized, for example, by the filtration through a bacteria-holding filter or heat sterilization. In the preparation of collyrium, pH value and ion strength of the agent are especially important, and they may be optionally adjusted to the optimal value depending on the types and amounts of other active ingredients or additives used.

The oculentum according to the present invention may contain vaseline, selen 50, plastibase, macrogols as a base, and surfactant such as polysorbate, Tween, purified lanolin, jelly such as carboxymethyl cellulose, methylcellulose, carboxyvinyl polymer to enhance hydrophilism.

The ocular hypotensive agent of the present invention may be used as a remedy for glaucoma utilizing its ocular hypotensive potency. When used as the remedie for treatment of glaucoma, the present agents may be compounded with the conventional cholinergic ocular hypotensive agent (e.g., pilocarpine, carbachol, which possesses excellent miotic activity) anticholinesterases (e.g., demecarium, D.F.P., echothiophate), physostigmine salicylate, pilocarpine hydrochloride as miotics, mannitol, glycerin, isosorbide as hyperosmotic agent for intravenous injection, chlorobutanol, benzalkonium chloride, propylparabene, methylparaben, ethylparaben, butylparaben as preservatives for collyrium, penicillin, sulfonamide, chloramphenicol, cortisone, chlorpheniramine for prevention and treatment of other inflammation.

The present invention will be illustrated in the following examples.

EXAMPLE 1

Preparations of 20-substituted-PGs; see Synthetic Chart I 1-1) Preparation of (1S,5R,6R,7R)-6-(3-oxo-(E)-1-decenyl)-7-(4-phenylbenzoyloxy)-2-oxabicyclo[3.3.0]octane-3-one (3):

Commercially available (−)-Corey lactone (1) (7.0 g) was subjected to Collins oxidation in dichloromethane to give aldehyde (2). The aldehyde (2) was reacted with anion obtained from dimethyl (2-oxononyl)phosphonate (4.97 g) to give the title compound (3). Yield: 5.71 g 1-2) Preparation of (1S,5R,6R,7R)-6-[3(S)-hydroxy-(E)-1-decenyl]-7-(4-phenylbenzoyloxy)-2-oxabicyclo[3.3.0]octane-3-one (4a):

The unsaturated ketone (3) (3.03 g) was dissolved into a mixed solvent of methanol (60 ml) and THF (7 ml). Into the obtained solution cerium (III) chloride.7H$_2$O (2.38 g) was added at −20° C., and stirred at the same temperature for 10 minutes, into which sodium borohydride (0.25 g) was added and stirred for 5 minutes. A crude compound obtained by a usual work-up was purified using a column chromatography to give the title compound (4a) as a compound having a lower polarity and the 3R-hydroxy compound (4b) of the title compound (4a) as a compound having a higher polarity. Yield: 4.58 g (4a:3S-hydroxy compound)

1-3) Preparation of (1S,5R,6R,7R)-7-(4-phenylbenzoyloxy)-6-[3(S)-(2-tetrahydropyranyloxy)-(E)-1decenyl]-2-oxabicyclo[3.3.0]octane-3-one (5):

The 3S-hydroxy compound (4a) (4.58 g) was dissolved into methylene chloride (100 ml), and reacted with dihydropyran in the presence of a catalytic amount of p-toluenesulfonic acid-1H$_2$O. After a usual work-up, the reaction mixture was column-chormatographed to give the title compound (5). Yield: 5.03 g 1-4) Preparation of (1S,5R,6R,7R)-7-hydroxy-6-[3(S)-(2-tetrahydropyranyloxy)-(E)-1-decenyl]-2-oxabicyclo[3.3.0]octane-3-one (6):

The tetrahydropyranyl ether (5) (5.03 g) was dissolved into a dry methanol (300 ml), into which potassium carbonate (1.49 g) was added, and stirred at room temperature for 6 hours. A crude compound obtained by a usual work-up was column-chromatographed to give the title compound (6). Yield: 3.25 g 1-5) Preparation of (1S,2RS,5R,6R,7R)-3,7-dihydroxy-6-[3(S)-(2)-tetrahydropyranyloxy)-(E)-1-decenyl]-2-oxabicyclo[3.3.30]octane (7):

Alcohol (6) (2.00 g) was reduced in dry toluene (40 ml) using DIBAL-H at −70° C. The lactol (7) was obtained by a usual work up.

1-6) Preparation of 20-ethyl-15S-(2-tetrahydropyranyloxy)-PGF$_2\alpha$(8):

In dimethyl sulfoxide the lactol (7) was reacted with an ylide prepared from (4carboxybutyl)triphenylphosphonium bromide (8.33 g). The title compound(s) was obtained by a usual work-up.

1-7) Preparation of 20-ethyl-15S-(2-tetrahydropyranyloxy)-PGF$_2\alpha$ isopropyl ester (9):

Carboxylic acid (8) was dissolved in acetonitrile (50 ml), into which DBU (1.1 g) and isopropyl iodide (2.5 g) were added. The mixture was stirred at 45° C. for 5 hours. A crude compound obtained by a usual work-up was column-chromatographed to give the title compound (9). Yield: 1.00 g 1-8) Preparation of 11R-(t-butyldimethylsiloxy)-20-ethyl-15S-(2-tetrahydropyranyloxy)-PF$_2\alpha$ isopropyl ester (10):

The isopropyl ester (9) (0.37 g) was dissolved into dry DMF (3 ml), and reacted with imidazole (0.059 g) and t-butyldimethylsilyl chloride (0.132 g). A crude compound obtained by a usual work-up was purified by a column chromatography to give the title compound (10). Yield: 0.26 g 1-9) Preparation of 11R-(t-butyldimethylsiloxy)-20-ethyl-15S-(2-tetrahydropyranyloxy)-PGE$_2$ isopropyl ester (11):

The 11-silyl ether (10) (0.303 g) in acetone (20 ml) was oxidized using Jones reagent at $-40°$ C. to give the title compound (11). Yield: 0.27 g 1-10) Preparation of 20-ethyl-PGE$_2$ isopropyl ester (12) and 20-ethyl-PGA$_2$ isopropyl ester (13):

11R-(r-butyldimethylsiloxy)-20-ethyl-15S-(2-tetrahydropyranyloxy)-PGE$_2$ isopropyl ester (11) (0.27 g) was stirred in a mixed solvent of acetic acid/water (7/1) (20 ml) at 65° C. for 15 hours. A crude product obtained by a concentration under reduced pressure was column-chromatographed to give the title compound (12) as a colorless oily compound (higher polarity) and the title compound (13) as a colorless oily compound (lower polarity). Yield of 20-ethyl-PGE$_2$ isopropyl ester (12) and 20-ethyl-PGA$_2$ isopropyl ester (13) are 0.040 g and 0.080 g respectively.

1-11) Preparation of 20-ethyl-PGF$_2\alpha$ isopropyl ester (14):

The 20-ethyl-15S-(2-tetrahydropyranyloxy)-PGF$_2°$ isopropyl ester (9) (0.60 g) was dissolved in a mixed solvent of acetic acid/water/THF (3/1/1) (20 ml), and maintained at 40°–45° C. for 3 hours. A crude product obtained by the concentration under reduced pressure was column-chromatographed to give the title compound (14) as a colorless solid material. Yield: 0.023 g The $^1$H NMR and Mass spectra of the 20-ethyl-PGF$_2\alpha$ isopropyl ester are shown hereinafter:

$^1$H NMR(CDCl$_3$) δ: 0.86(3H,t,J=6Hz), 1.18(6H,d,J=7Hz), 1.10–2.60(26H,m), 3.17(1H,m), 3.70–4.23(3H,m), 4.95(1H,hept,J=7Hz), 5.20–5.60(4H,m)

Mass(EI) m/z 424(M+), 406(M+H$_2$O), 388(M+-2H$_2$O), 370(M+-3H$_2$O)

The $^1$H NMR and Mass spectra of the 20-ethyl-PGE$_2$ isopropyl ester are shown hereinafter:

$^1$H NMR(CDCl$_2$) δ: 0.88(3H,t,J=5Hz), 1.23(6H,d,J=7Hz), 1.04–2.90(25H,m), 3.11(1H,m), 3.85–4.23(2H,m), 4.96(1H,hept,J=7Hz), 5.33(2H,m), 5.58(2H,m)

Mass(EI) m/z 422(M+), 404(M+-H$_2$O), 386(M+-2H$_2$O), 345(M+-H$_2$O-iC$_3$H$_7$O)

The $^1$H NMR and Mass Spectra of 20-ethyl-PGA$_2$ isopropyl ester are shown hereinafter:

$^1$H NMR(CDCl$_2$) δ: 0.73–1.05(3H,m), 1.21(6H,d,J=6Hz), 1.03–2.70(22H,m), 3.19(1H,m), 4.05(1H,m), 4.96(1H,hept,J=6Hz), 5.36(2H,m), 5.56(2H,m), 6.14(1H,d,J=6Hz), 7.46(1H,dd,J=6Hz,J=2.5Hz)

Mass(EI) m/z 404(M+), 386(M+-H$_2$O), 345(M+-i-C$_3$H$_2$O), 327(M+-H$_2$O-i-C$_3$H$_7$O)

The $^1$H NMR spectra were recorded on HITACHI R-90H (available from K. K. Hitachi Seisaku-sho) using heavy chloroform as a solvent.

Mass spectrography was measured by Mass spectrometer M-80B (available from K. K. Hitachi Seisaku-sho) with a direct inlet system at 70 eV of ionizing potential.

EXAMPLE 2

Preparation of 15-keto-20-substituted-PGs

1. Preparation of 15-keto-20-ethyl-PGF$_2\alpha$-isopropyl ester (10') (see Synthetic Chart II):

1-1) Preparation of (1S,5R,6R,7R)-6-(3-oxo-(E)-1-decenyl)-7-(4-phenylbenzoyloxy)-2-oxabicyclo[3.3.-0]octane-3one (3'):

Commercially available (−)-Corey lactone (1) (7 g) was subjected to Collins oxidation in dichloromethane to give aldehyde (2'). The aldehyde (2') was reacted with dimethyl (2-oxononyl)phosphonate (4.97 g) anion to give the title compound (3').

1-2) Preparation of (1S,5R,6R,7R)-6-[3,3-ethyleneoxy-(E)-1-decenyl]-7-(4-phenylbenzoyloxy)-2oxabicyclo[3.3.0]octane-3-one (4'):

The unsaturated ketone (3') (2.0 g) obtained in the above process was refluxed overnight with ethylene glycol (12 g) in benzene (100 ml) in the presence of a catalytic amount of p-toluene sulfonic acid·$^1$H$_2$O while removing the generating water. The reaction mixture was chromatographed (hexane/ethyl acetate=2-/1–1/1) to give the title compound (4'). Yield: 1.98 g 1-3) Preparation of (1S,5R,6R,7R)-6-[3,3-ethylenedioxy-(E)-1-decenyl]-7-hydroxy-2-oxabicyclo[3.3.0]octane-3-one (5'):

The ketal (4') (1.98 g) was treated with potassium carbonate (0.6 g) in methanol (50 ml) to give the title alcohol (5'). Yield: 1.12 g 1-4) Preparation of (1S,5R,6R,7R)-6-[3,3-ethylenedioxy-(E)-1-decenyl]-7-(2-tetrahydropyranyloxy)-2-oxabicyclo[3.3.0]octane (6'):

The alcohol (5') obtained in the above process (1-3) (0.88 g) was reacted with dihydropyran in the presence of a catalytic amount of pyridium p-toluenesulfonate in methylene chloride (50 ml) to give the title compound tetrahydropyranyl ether (6'). Yield: 1.07g 1-5) Preparation of (1S,2RS,5R,6R,7R)-6-[3,3-ethylenedioxy-(E)-1-decenyl]-2-hydroxy-7-(2-tetrahydropyranyloxy)-2-oxabicyclo[3.3.0]octane (7'):

The tetrahydropyranyl ether (6') (1.07) was reduced using DIBAL-H in toluene (20 ml) at $-70°$ C. The resultant was worked up according to a usual manner to give the title compound lactol (7').

1-6) Preparation of 15,15-ethylenedioxy-20-ethyl-11R-(2-tetrahydropyranyloxy)-PGF$_2\alpha$ (8'):

The lactol (7') was reacted with an ylide prepared from (4-carboxybutyl)triphenylphosphonium bromide (4.5 g) and sodium hydride in dimethyl sulfoxide at room temperature. According a usual work-up the title compound carboxylic acid (8') was obtained.

1-7) Preparation of 15,15-ethylenedioxy-20-ethyl-11R-(2-tetrahydropyranyloxy)-PGF$_2\alpha$ isopropyl ester (9'):

The title compound isopropyl ester (9') was prepared by esterifying the carboxylic acid (8') using isopropyl iodide and DBU in acetonitrile (20 ml). Yield: 1.0 g 1-8) Preparation of 15-keto-20-ethyl-PGF$_2\alpha$ isopropyl ester (10'):

15,15-ethylenedioxy-20-ethyl-11R-(2-tetrapyranyloxy)-PGF$_2\alpha$ isopropyl ester (9) (0.195 g) was added into a mixed solvent of acetic acid/THF/water (3/1/1) (15 ml), and held at 40°–50° C. for 3 hours. A crude compound obtained by the concentration of the reaction mixture under reduced pressure was chromatographed to give the title compound (10') as a colorless oily product. Yield: 0.142 g The $^1$H NMR and Mass spectra of the title compound (10') is as follow:

$^1$H NMR (CDCl$_2$) δ: 0.87(3H,t,J=6Hz), 1.10(6H,d,J=7Hz), 1.05–2.65(26H,m), 4.05(1H,m), 4.19(1H,m), 4.96(1H,hept,J=6Hz), 5.34(2H,m), 6.12(1H,d,J=16Hz), 6.65(1H,dd,J=16Hz,J=9Hz)

Mass(EI) m/z 422(M+), 404(M+-H$_2$O), 386(M+-2H$_2$O), 360, 345

(2) Preparation of 15-keto-20-ethyl-PGE$_2$ isopropyl ester (12'):

2-1) 15,15-ethylenedioxy-20-ethyl-11R-(2tetrahydropyranyloxy)-PGE$_2$ isopropyl ester (11'):

The compound (9') obtained by the above process (1–7) (0.311 g) was oxidized with Jones reagent at −40° C. in acetone (15 ml) to give the title compound (11'). Yield: 0.245 g 2-2) Preparation of 15-keto-20-ethyl-PGE$_2$ isopropyl ester (12'):

The compound (11') (0.240 g) was added to a mixed solvent of acetic acid/THF/water (3/1/1) (15 ml), and held at 35°–45° C. for 2 hours. A crude compound obtained by the concentration of the resultant under reduced pressure was chromatographed to give the title compound (12') as a colorless oily product. Yield: 0.148 g The $^1$H NMR and Mass spectra of the obtained 15-keto-20-ethyl-PGE$_2$ isopropyl ester (12') are as follows:

$^1$H NMR(CDCl$_2$) δ: 0.87(3H,t,J=6Hz), 1.20(6H,d,J=6Hz), 1.03–2.95(25H,m), 4.01–4.38(1H,m), 4.94(1H,hept,J=6Hz), 5.32(2H,m), 6.21(1H,d,J=16Hz), 6.71(1H,dd,J=16Hz,J=8Hz)

Mass(EI) m/z 420(M+), 402(M+-H$_2$O), 343(M+-H$_2$O-i-C$_3$H$_7$)

(3) Preparation of 15-keto-20-ethyl-PGA$_2$ isopropyl ester (23') (see Synthetic Chart III):

3-1) Preparation of (1S,5R,6R,7R)-6-[3(S)-hydroxy-(E)-1-decenyl]-7-(4-phenylbenzoyloxy)-2-oxabicyclo[3.3.0]octane-3-one (13'):

Into a mixed solvent of dry THF (7 ml) and dry methanol (60 ml) was dissolved the α,β-unsaturated ketone (3') (3.03 g), to which cerium chloride (2.38 g) was added. The mixture was stirred at −20° C. for 10 minutes, and sodium borohydride (0.249 g) was added, and stirred for minutes. The resultant was treated with a usual work-up, and then the obtained crude compound was chromatographed to give 3S-hydroxylcompound (1.18 g) and mixture of 3S- and 3-Rhydroxyl compound (1.39 g).

The mixture of 3S-hydroxyl compound and 3R-hydroxyl compound (1.39 g) was oxidized with Jones reagent to recover an α,β-unsaturated ketone (3'), which was subjected to a reduction process again. This process was repeated to give 3S-hydroxyl compound (13') 4.58 g (total).

3-2) Preparation of (1S,5R,6R,7R)-7-(4-phenylbenzoyloxy)-6-[3(S)-(2-tetrahydropyranyloxy)-(E)-1decenyl]-2-oxabicyclo[3.3.0]octane-3-one (14'):

The alcohol (13') (4.58 g) was treated with dihydropyran in dry methylene dichloride (100 ml) in the presence of a catalytic amount of p-toluene sulfonic acid-1H$_2$O to give the title compound tetrahydropyranyl ether (14'). Yield: 5.03 g 3-3) Preparation of (1S,5R,6R,7R)-7-hydroxy-6-[3(S)-(2-tetrahydropyranyloxy)-(E)-1-decenyl]-2-oxabicyclo[3.3.0]octane-3-one (15'):

The tetrahydropyranyl ether (14') (5.03 g) was stirred with potassium carbonate (1.49 g) in dry methanol (300 ml) at room temperature for 6 hours to give the title compound (15'). Yield: 3.25 g 3-4) Preparation of (1S,5R,6R,7R)-2,7-dihydroxy-6-[3(S)-(2-tetrahydropyranyloxy)-(E)-1-decenyl]-2-oxabicyclo[3.3.0]octane (16')

The alcohol (15') was reduced using DIBAL-H at −78° C. in toluene (60 ml) to give the title compound lactol (16').

3-5) Preparation of 15S-(2-tetrahydropyranyloxy)-20-ethyl-PGF$_2$α (17'):

The lactol (16') was reacted with an ylide prepared from (4-carboxybutyl)triphenyl phosphonium bromide (13.5 g) and sodium hydride in dimethyl sulfoxide at room temperature over night. According to a usual work-up the title compound (17') was obtained. Yield: 4.53 g 3-6) Preparation of 15S-(2-tetrahydropyranyloxy)-20-ethyl-PGF$_2$α isopropyl ester (18'):

The obtained carboxylic acid (17') (2.8 g) was esterified with isopropyl iodide (2.5 g) and DBU (1.1 g) in acetonitrile (50 ml) at 45° C. for 5 hours to give the title compound isopropyl ester (18'). Yield: 1.0 g 3-7) Preparation of 15S-(2-tetrahydropyranyloxy)-20-ethyl-11R-(t-butyldimethylsilyloxy)-PGF$_2$α isopropyl ester (19'):

The diol (18') (0.37 g) obtained in the process (3–6) treated with t-butyldimethylsilyl chloride (0.132 g) and imidazole (0.0594 g) in DMF (3 ml) to give the title compound silyl ether (19'). Yield: 0.26 g 3-8) Preparation of 15S-(2-tetrahydropyranyloxy)-20-ethyl-11R-(t-butyldimethylsilyloxy)-PGE$_2$α isopropyl ester (20'):

The silyl ether (19') (0.302 g) was oxidized using Jones reagent at −40°−−35° C. in acetone (20 ml) to give the title compound 20'). Yield: 0.27 g 3-9) Preparation of 20-ethyl-PGA$_2$ isopropyl ester (22') and 20-ethyl-PGE$_2$ isopropyl ester (21'):

The compound (20') (0.27 g) obtained in the process of (3-8) was dissolved in acetic acid 70% solution (23 ml), and kept at 65° C. for 15 hours. A crude product obtained by the concentration of the resultant under a reduced pressure was chromatographed to give the compound (22') (Yield: 0.080 g) and the compound (21') (0.040 g).

3-10) Preparation of 15-keto-20-ethyl-PGA$_2$ isopropyl ester (23'):

The obtained compound (22') (0.025 g) was oxidized with Jones reagent at −40°−−35° C. in acetone (5 ml) to give the title compound (23'). Yield: 0.023 g The $^1$H NMR spectrum of the 15-keto-20-ethyl-PGA$_2$ isopropyl ester (23') is as follow:

$^1$H NMR(CDCl$_2$) δ: 0.87(3H,t,J=5.5Hz), 1.22(6H,d,J=7Hz), 1.03–2.75(25H,m), 3.35(1H,m), 4.96(1H,hept,J=7Hz), 5.37(2H,m), 6.12(1H,d,J=16Hz), 6.23(1H,dd,J=6Hz), 6.69(1H,dd,J=16Hz,J=7.5Hz), 7.46(1H,dd,J=6Hz,J=2.5Hz)

The $^1$H NMR spectra were recorded on HITACHI R-90H (available from K. K. Hitachi Seisakusho) using heavy chloroform as a solvent.

Mass spectrography was measured by Mass spectrometer.M-80B (available from K.K. Hitachi Seisakusho) with a direct inlet system at 70 eV of ionized potential.

EXAMPLE 3

Evaluation of Intraocular Pressure and Hyperemia

For the purpose of tonometry, Japanese White male rabbits (2.0–3.0 Kg) were fixed in rabbit holders. After topical anesthetization with 0.4% oxybuprocaine hydrochloride, intraocular pressure was measured using a pheumatic applanation tonometer (manufactured by Japan Alcon). After the topical application of 50 μl of the suspensions of the test drugs in a physiological saline to one eye, the intraocular pressure was measured and the intraocular pressure reduction (%) caused by each test drug was calculated. At the same time, the extent of conjunctival hyperemia was observed. The results are shown in Table 1.

TABLE 1

| Test Drug | Dose (μg/eye) | Percentage of Change of IOP | Hyperemia |
|---|---|---|---|
| 1 | 25 | 27 | + |
| 2 | 25 | 37 | ++ |
| 3 | 25 | 10 | +– |
| 4 | 25 | 15 | +– |

TABLE 1-continued

| Test Drug | Dose (μg/eye) | Percentage of Change of IOP | Hyperemia |
|---|---|---|---|
| 5 | 25 | 20 | +– |
| 6 | 25 | 30 | + |
| 7 | 25 | 10 | – |
| 8 | 25 | — | — |
| 9 | 25 | — | — |
| 10 | 100 | 46 | +++* |
| 11 | 25 | 31 | +++* |
| 12 | 10 | 32 | +++* |

–: none
+–: barely visible hyperemia
+: slight hyperemia
++: moderate hyperemia
+++: severe hyperemia
*lid-closing and severe hyperemia are observed.

Test Drug
1. 20-ethyl-$PGF_{2\alpha}$ isopropyl ester
2. 20-ethyl-$PGE_2$ isopropyl ester
3. 20-ethyl-$PGA_2$ isopropyl ester
4. 15-keto-20-ethyl-$PGF_{2\alpha}$
5. 15-keto-20-ethyl-$PGF_{2\alpha}$ isopropyl ester
6. 15-keto-20-ethyl-$PGE_2$ isopropyl ester
7. 15-keto-20-ethyl-$PGA_2$ isopropyl ester
8. 15-keto-$PGF_{2\alpha}$
9. 15-keto-$PGE_2$
10. $PGF_{2\alpha}$
11. $PGF_{2\alpha}$ isopropyl ester
12. $PGE_2$

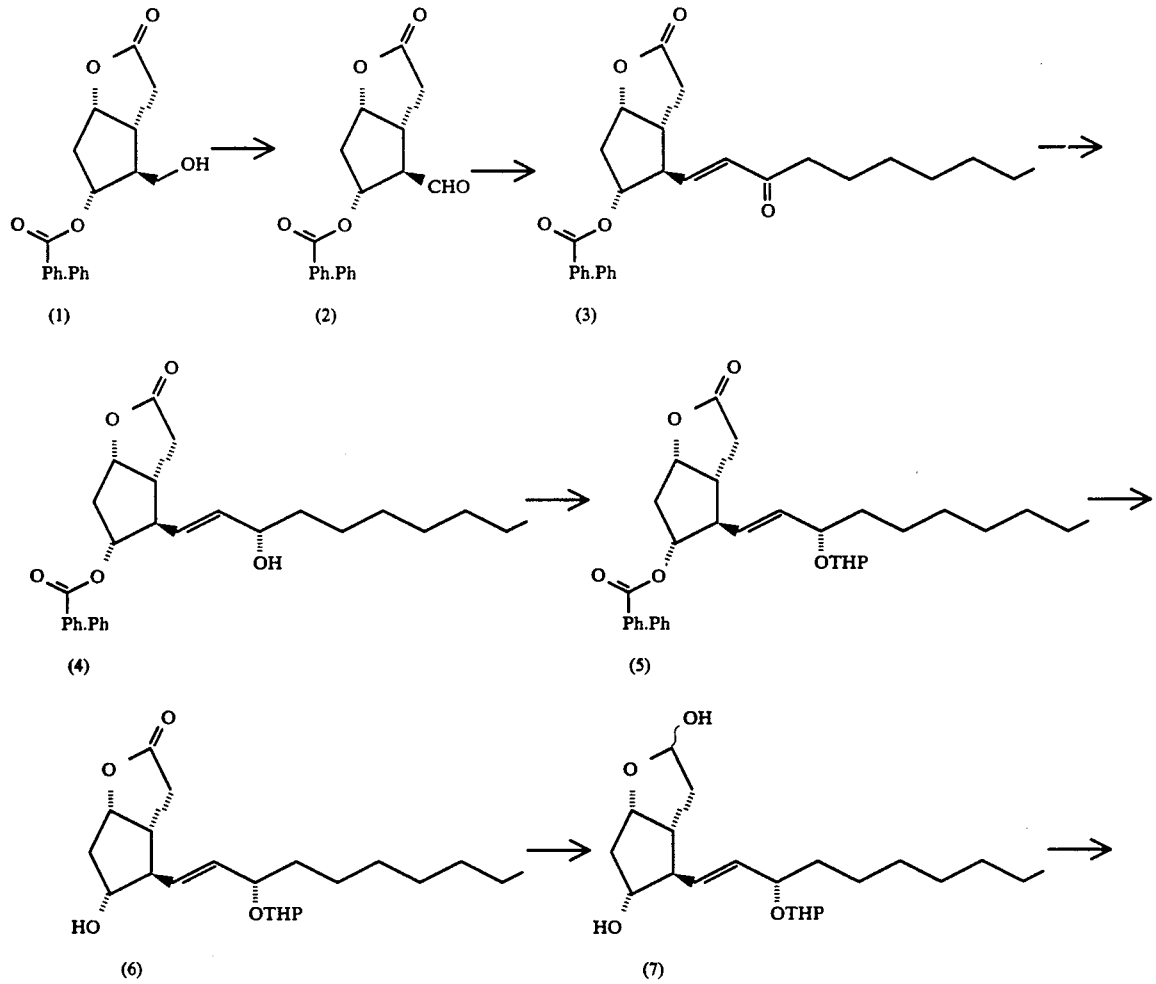

Synthetic Chart I

-continued
Synthetic Chart I
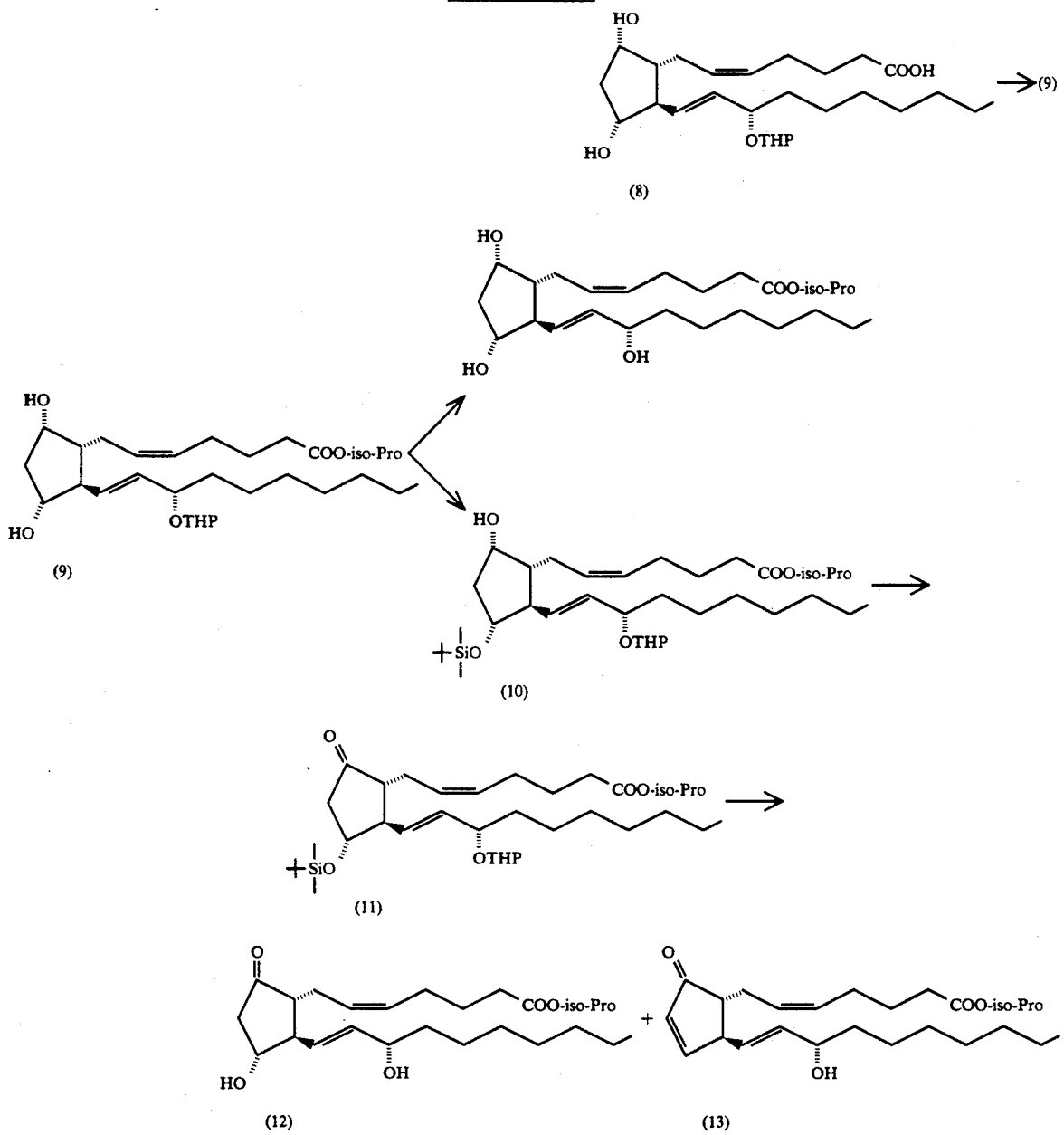
Synthetic Chart II
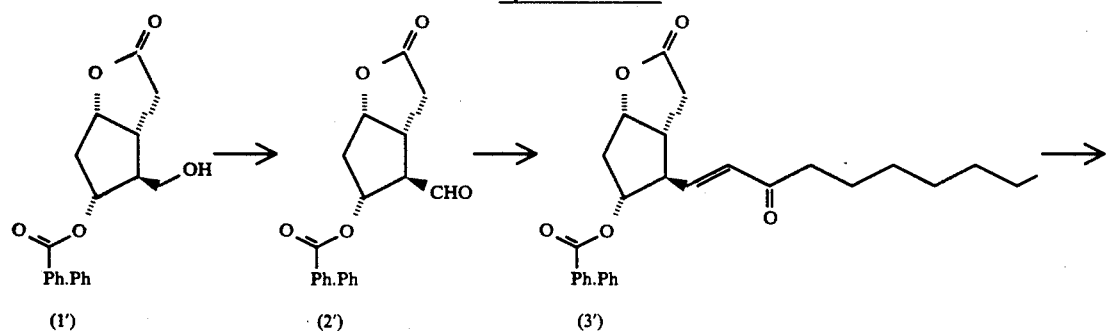

-continued
Synthetic Chart II
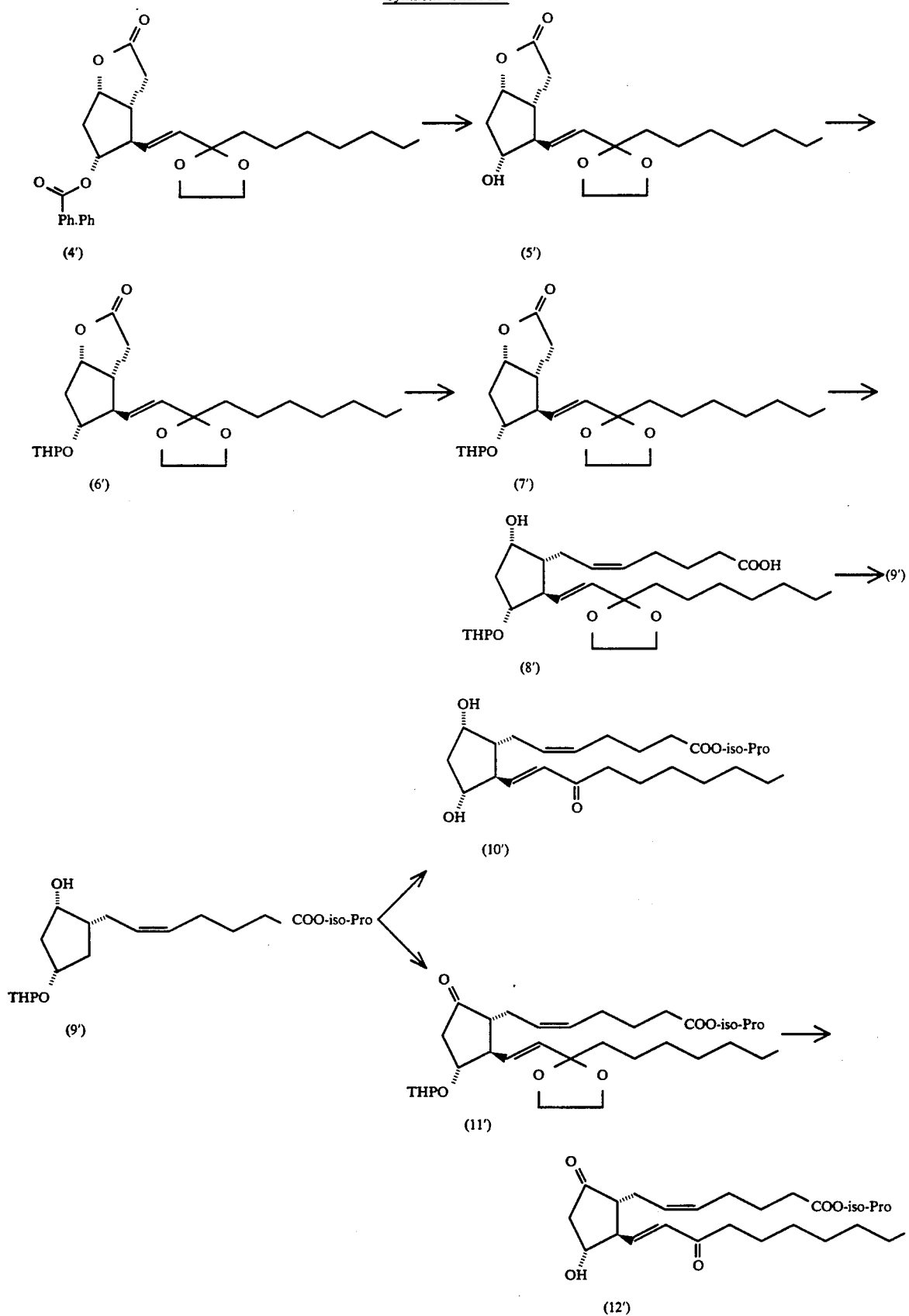

Synthetic Chart III
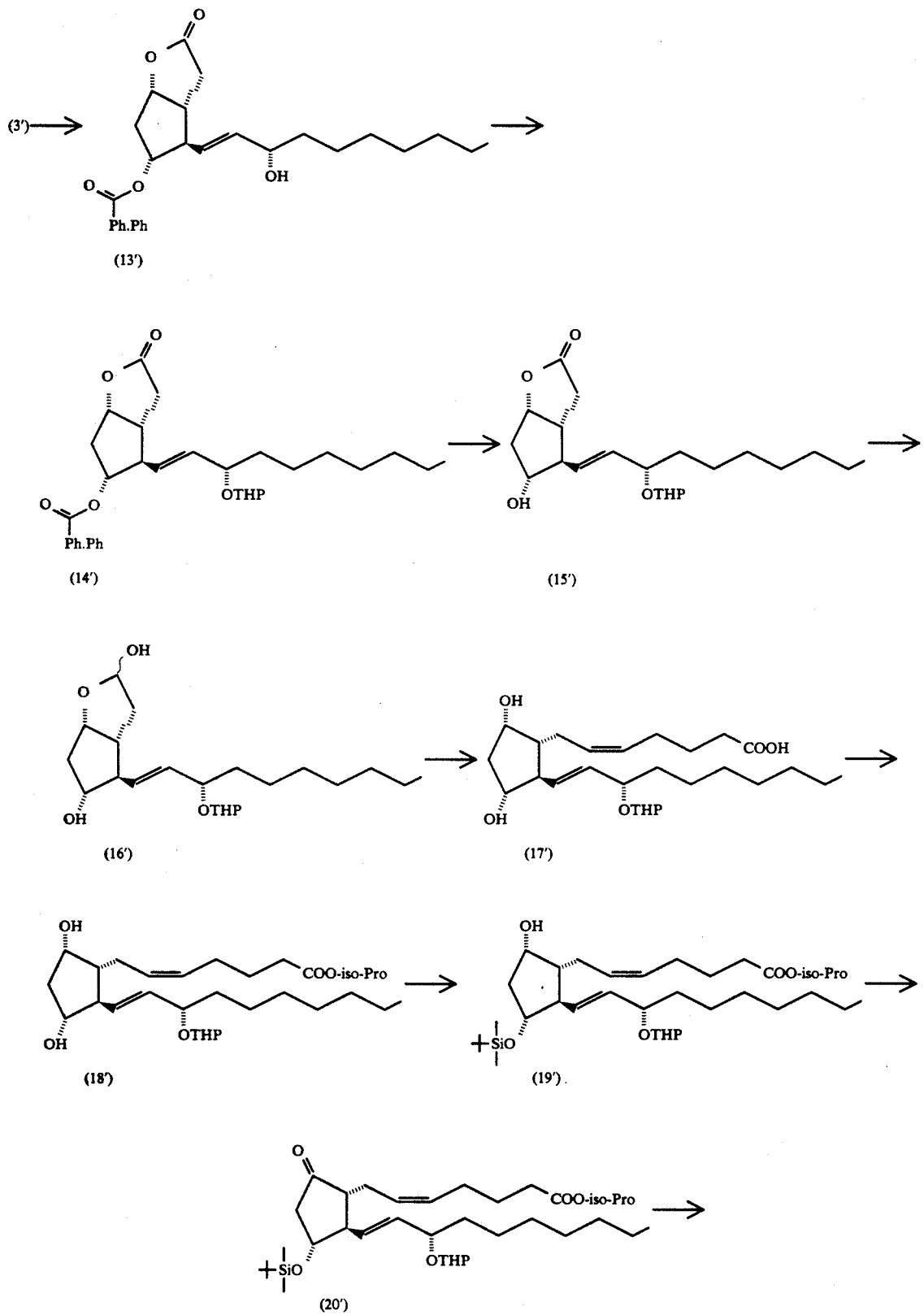

-continued
Synthetic Chart III

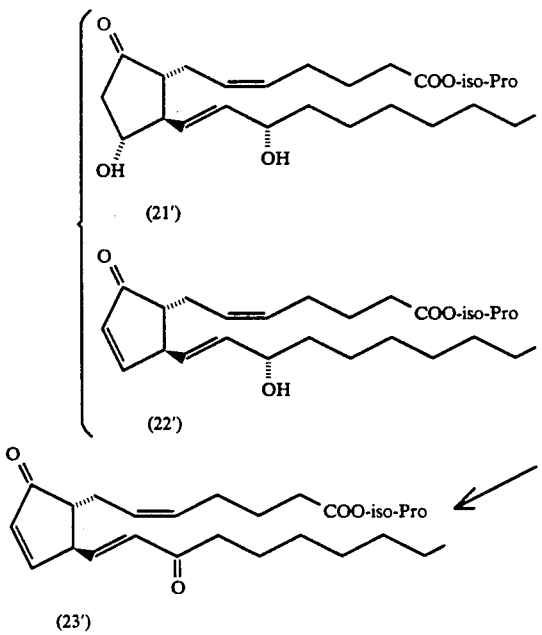

What is claimed is:

1. A method for treating ocular hypertension in a patient needing such treating which comprises administering to said patient an amount of a prostaglandin effective to treat ocular hypertension, wherein the prostaglandin is represented by formula (I):

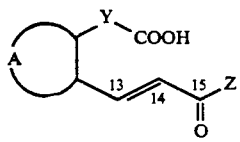

wherein, A is

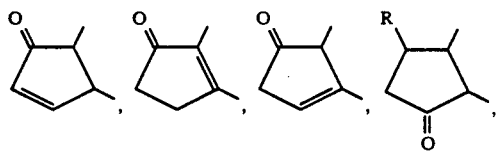

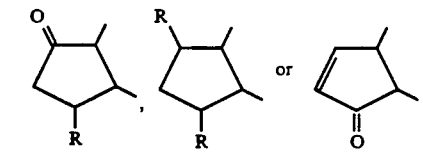

(in which R is hydroxy, hydroxy $C_1$-$C_3$ alkyl or $C_1$-$C_2$ alkyl); Y is a saturated or unsaturated $C_{2\text{-}6}$ hydrocarbon chain; Z is a saturated or unsaturated $C_{7\text{-}9}$ (aliphatic) hydrocarbon straight chain; or a physiologically acceptable salt or esterified carboxyl group derivative selected from the group consisting of $C_{1\text{-}8}$ alkyl, $C_{3\text{-}6}$ cycloalkyl, benzyl, phenyl, $C_{1\text{-}3}$ hydroxyalkyl, $C_{1\text{-}2}$ alkoxy $C_{1\text{-}3}$ alkyl, tri $C_{1\text{-}2}$ alkylsilyl, and tetrahydropyranyl.

2. The method of claim 1, wherein the esterified carboxyl group derivative is a $C_1$-$C_4$ alkyl group.

3. The method of claim 1, wherein the Z is represented by a formula (II):

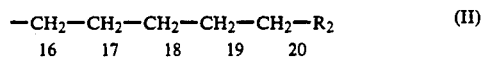

(in which $R_2$ is a $C_{2\text{-}4}$ alkyl group).

4. The method of claim 3, wherein the $R_2$ is an ethyl group.

5. The method for treating glaucoma in a patient needing such treatment which comprises administering to said patient an amount of a prostaglandin effective to treat glaucoma, wherein the prostaglandin is represented by a formula (I):

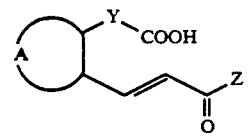

wherein, A is

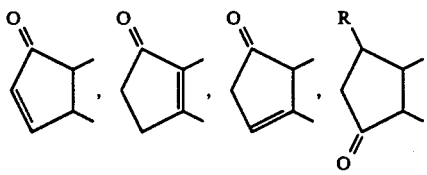

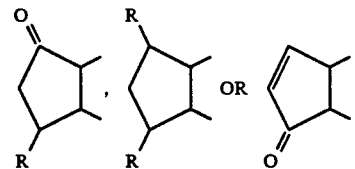

(in which R is hydroxy, hydroxy $C_1$-$C_3$ alkyl or $C_1$-$C_2$ alkyl); Y is a saturated or unsaturated $C_{2\text{-}6}$ hydrocarbon chain; Z is a saturated or unsaturated $C_{7\text{-}9}$ (aliphatic) hydrocarbon straight chain; or a physiologically acceptable salt or esterified carboxyl group derivative selected from the group consisting of $C_{1-8}$ alkyl, $C_{3-6}$ cycloalkyl, benzyl, phenyl, $C_{1-3}$ hydroxyalkyl, $C_{1-2}$ alkoxy $C_{1-3}$ alkyl, tri $C_{1-2}$ alkylsilyl, and tetrahydropyranyl.

6. An ocular hypotensive composition comprising an amount of a prostaglandin effective as an ocular hypotensive agent and a pharmaceutically acceptable carrier, wherein the prostaglandin is represented by a formula (IV):

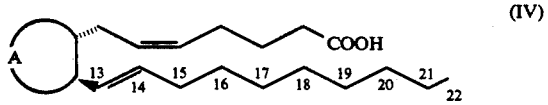

wherein, A is

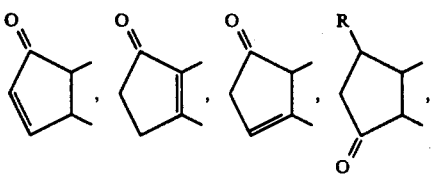

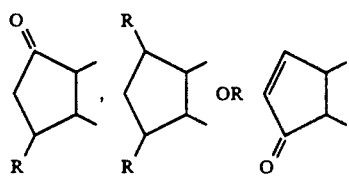

(in which R is hydroxy, hydroxy $C_1$–$C_3$ alkyl or $C_1$–$C_2$ alkyl); or a physiologically acceptable salt or a $C_{1-4}$ alkyl ester.

7. The composition of claim 6, wherein the A is

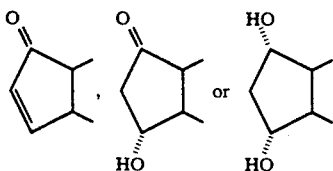

8. A method for treating ocular hypertension in a patient needing such treating which comprises administering to said patient an amount of a 13,14-unsaturated-15-keto-prostaglandin A, E or F having a $C_2$–$C_4$ alkyl group substituent at the 20-position effective to treat ocular hypertension.

9. The method of claim 8, wherein the carboxyl group at the end of the α-chain in the 13,14-unsaturated-15-keto-prostaglandin A, E or F having a $C_2$–$C_4$ alkyl group substituent at the 20-position is in the form of an alkyl ester.

10. The method of claim 8, wherein the 13,14-unsaturated-15-keto-prostaglandin A, E or F having a $C_2$–$C_4$ alkyl group substituent at the 20-position is a 13,14-unsaturated-15-keto-20-ethyl-prostaglandin A, E or F.

11. A method for treating glaucoma in a patient needing such treating which comprises administering to said patient an amount of a 13,14-unsaturated-15-keto-prostaglandin A, E or F having a $C_2$–$C_4$ alkyl group substituent at the 20-position effective to treat glaucoma.

12. An ocular hypotensive composition comprising an amount of a 13,14-unsaturated-15-keto-prostaglandin A, E or F effective as an ocular hypotensive agent and a pharmaceutically acceptable carrier.

13. A method for treating ocular hypertension in a patient needing such treating which comprises administering to said patient an amount of a prostaglandin effective to treat ocular hypertension, wherein the prostaglandin is represented by a formula (II):

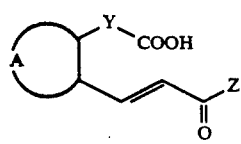

wherein, A is

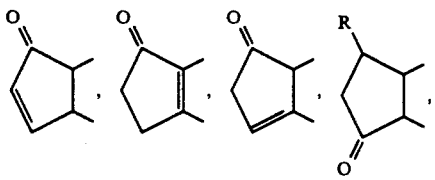

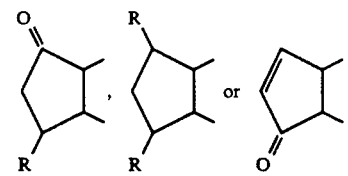

(in which R is hydroxy, hydroxy $C_1$–$C_3$ alkyl or $C_1$–$C_2$); Y is a saturated or unsaturated $C_{2-6}$ hydrocarbon chain; Z is a $C_7$–$C_9$ saturated or unsaturated aliphatic, alicyclic, aralkyl or aromatic hydrocarbon; or a physiologically acceptable salt or esterified carboxyl group derivative thereof.

* * * * *